United States Patent [19]

Ryu et al.

[11] 4,370,245

[45] Jan. 25, 1983

[54] GREASE COMPOSITIONS CONTAINING QUATERNARY AMMONIUM THIOMOLYBDATES

[75] Inventors: Yumi P. Ryu, Murrysville; James R. Anglin, Gibsonia; Gary M. Singerman, Monroeville, all of Pa.

[73] Assignee: Gulf Research & Development Company, Pittsburgh, Pa.

[21] Appl. No.: 219,926

[22] Filed: Dec. 24, 1980

Related U.S. Application Data

[63] Continuation-in-part of Ser. No. 213,676, Dec. 5, 1980, Pat. No. 4,343,747, which is a continuation-in-part of Ser. No. 214,972, Dec. 10, 1980, Pat. No. 4,343,746.

[51] Int. Cl.$^3$ .............................................. C10M 1/32
[52] U.S. Cl. .............................. 252/46.4; 252/51.5 A
[58] Field of Search ......................... 252/46.4, 51.5 A

[56] References Cited

U.S. PATENT DOCUMENTS

| | | | |
|---|---|---|---|
| 2,909,541 | 10/1959 | Hugel | 252/46.4 |
| 2,938,869 | 5/1960 | Hugel | 252/46.4 |
| 4,104,177 | 8/1978 | Caruso | 252/51.5 A |
| 4,111,822 | 9/1978 | Caruso | 252/51.5 A |

Primary Examiner—Jacqueline V. Howard
Attorney, Agent, or Firm—Deane E. Keith; Forrest D. Stine; Donald L. Rose

[57] ABSTRACT

The presence of a minor amount of a tetrahydrocarbylammonium thiomolybdate containing at least about 15 carbon atoms, such as trioctylmethylammonium thiomolybdate, to a grease thickened with a substituted-urea composition substantially improves the extreme pressure properties of the grease.

16 Claims, No Drawings

GREASE COMPOSITIONS CONTAINING QUATERNARY AMMONIUM THIOMOLYBDATES

This application is a continuation-in-part of U.S. Ser. No. 213,676 filed Dec. 5, 1980, U.S. Pat. No. 4,343,747, and U.S. Ser. No. 214,972, filed Dec. 10, 1980, U.S. Pat. No. 4,343,746.

SUMMARY OF THE INVENTION

This invention relates to grease compositions having improved extreme pressure properties comprising a base oil, a substituted-urea thickener and a minor amount of a quaternary ammonium thiomolybdate, more specifically described as a tetrahydrocarbylammonium thiomolybdate.

DESCRIPTION OF THE INVENTION

In the preparation of greases, lubricating oils are generally thickened with fatty acid soaps, in particular the alkali metal and alkaline earth metal soaps. Many other types of thickening agents have been proposed some of which have been used to a modest extent. Thickeners involving aryl-substituted mono- and di-ureas are described in U.S. Pat. Nos. 2,710,839; 2,710,840 and 2,710,841. Various polyurea thickeners containing from two to about eight ureido groups and various alkyl or aryl radicals are described in U.S. Pat. Nos. 2,832,739 and 3,243,372. U.S. Pat. No. 4,065,395 describes a grease composition having improved high temperature properties as the result of a specially defined aryldiurea thickener composition prepared by the reaction of p-toluidine and p-chloroaniline with a toluene diisocyanate in specified proportions. These substituted-urea thickeners, also variously called polyurea thickeners and ureido thickeners, are characterized by the presence of at least one divalent ureido radical, —NH.CO.NH—, in the compound.

In accordance with our invention we have discovered that certain tetrahydrocarbylammonium thiomolybdates substantially enhance the extreme pressure (e.p.) properties of substituted-urea thickened greases. This is surprising because the same thiomolybdates do not effect an e.p. improvement when tested in greases thickened with alkali metal or alkaline earth metal soaps. It is further surprising because different tetrahydrocarbylammonium thiomolybdates are not effective with the substituted-urea thickened greases.

The quaternary ammonium thiomolybdates which are useful for improving the extreme pressure properties of greases thickened with substituted-urea compounds are defined by the following formula:

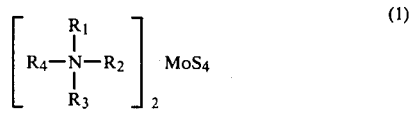

where $R_1$, $R_2$ and $R_3$ are independently selected from alkyl and alkenyl having from 1 to about 30 carbon atoms, preferably 1 to about 20 carbon atoms; $R_4$ is selected from alkyl and alkenyl having from about 4 to about 30 carbon atoms, preferably about 4 to about 20 carbon atoms, and benzyl; and the total number of carbon atoms in $R_1$, $R_2$, $R_3$ and $R_4$ is at least about 15, preferably at least about 20, and most preferably at least about 24 carbon atoms, and no higher than about 80, preferably no higher than about 60 carbon atoms.

Examples of suitable quaternary ammonium thiomolybdates which are useful in accordance with our invention include
tetrabutylammonium thiomolybdate,
tetrapentylammonium thiomolybdate,
tetrahexylammonium thiomolybdate,
dodecyltrimethylammonium thomolybdate,
didodecyldimethylammonium thiomolybdate,
trioctylmethylammonium thiomolybdate,
hexadecyltrimethylammonium thiomolybdate,
dicocodimethylammonium thiomolybdate,
ditallowdimethylammonium thiomolybdate,
distearyldimethylammonium thiomolybdate,
bis(hydrogenated-tallow)dimethylammonium thiomolybdate,
octadecyltrimethylammonium thiomolybdate,
soyatrimethylammonium thiomolybdate,
tallowtrimethylammonium thiomolybdate,
tris(hydrogenated-tallow)methylammonium thiomolybdate,
disoyadimethylammonium thiomolybdate,
stearylbenzyldimethylammonium thiomolybdate,
dodecylbenzyldimethylammonium thiomolybdate,
dioctadecyldimethylammonium thiomolybdate, and the like. Moreover, many additional useful compounds as defined by the above formula are not specifically set out herein.

Mixtures of tetrahydrocarbylammonium thiomolybdates having different alkyl and/or alkenyl groups as defined above are also included herein whether prepared by mixing together two or more different tetrahydrocarbylammonium thiomolybdates or prepared from a mixture of precursor compounds, such as the reaction of a mixture of tetrahydrocarbylammonium salts with a thiomolybdate salt. Since the alkyl and alkenyl groups can be derived from the naturally occurring mixtures of fatty acids in animal or vegetable fats and oils, the term alkenyl includes mono-, di- and tri-olefinic groups.

The quaternary ammonium thiomolybdates which are useful herein are waxy, semi-solid to solid compounds with a brick red to dark red color. They decompose at a temperature between about 170° to about 200° C., depending on the specific compound, turning black upon decomposition. These thiomolybdates are used in an amount sufficient to improve the extreme pressure properties of the grease. More specifically they can be used in the grease in an amount between about 0.1 to about ten weight percent, but superior results are generally obtained in the preferred range of between about 0.5 to about five weight percent. The mechanism of their activity in improving the extreme pressure properties of substituted-urea thickened greases is not understood.

The tetrahydrocarbylammonium thiomolybdates can be prepared by the reaction of the corresponding quaternary ammonium salt such as the halide or sulfate with an alkali metal thiomolybdate. Since the alkali metal thiomolybdate is soluble in water and since most of the quaternary ammonium salts corresponding to the tetrahydrocarbylammonium thiomolybdate of formula (1) are not soluble in water, we have found that these water-insoluble quaternary ammonium salts can be dissolved in an organic solvent such as toluene or methylene chloride and reacted by agitating this solution and the aqueous alkali metal thiomolybdate in a two-phase reaction. The resulting tetrahydrocarbylammonium thiomolybdate product is dissolved in the organic solvent from which it is separated. The by-product alkali metal salt is removed in the aqueous phase. When the quaternary ammonium salt is soluble in water, which is the case with salts having a relatively low number of carbon atoms in the molecule, such as hexadecyltrimethylammonium chloride, the reaction can be carried out in a single-phase, aqueous reaction. The alkali metal thiomolybdate can be prepared by reacting an alkaline aqueous solution of an alkali metal molybdate with hydrogen sulfide gas.

The naturally occurring fatty acids are an excellent and convenient source for the higher molecular weight alkyl and alkenyl groups in the quaternary ammonium thiomolybdate. The unsaturated fatty acids can be converted to the corresponding alkenyl groups and they can be saturated, if desired, by conventional hydrogenation procedures. For example, oleic acid can be converted to octadecenyl and this can be hydrogenated to octadecyl. Since the naturally occurring fats comprise mixtures of two and generally more carbon chains of different lengths, the resulting quaternary ammonium compounds contain the alkenyl and/or alkyl groups in the same relative proportion as the precursor acids occur in the fat. The relative proportion of hydrocarbyl groups of various chain lengths that are derived from different natural sources referred to herein is set out in the following table in which coco is derived from coconut oil, tallow and stearyl are derived from beef fat and soya is derived from soya bean oil.

TABLE I

| chain length | coco | tallow | stearyl | soya |
|---|---|---|---|---|
| $C_8$ | 5 | — | — | — |
| $C_{10}$ | 8 | — | — | — |
| $C_{12}$ | 50 | — | — | — |
| $C_{14}$ | 18 | 5 | — | — |
| $C_{16}$ | 8 | 30 | 8 | 15 |
| $C_{17}$ | — | — | 1 | — |
| $C_{18}$ | 11 | 65 | 91 | 85 |

The grease composition having the improved extreme pressure properties of our invention can desirably be prepared from a hydrocarbon petroleum oil of lubricating grade and viscosity as customarily used in compounding greases. Suitable hydrocarbon mineral oils of lubricating grade and viscosity can also be obtained from shale oil, tar sands, coal oil, and the like. Or the lubricating oil can be a synthetic hydrocarbon oil, such as is obtained by the polymerization of olefins, particularly 1-olefins, to the lubricating range including the trimer, tetramer and pentamer of 1-decene and the like. Other synthetic oils which can be used as the base oil include propylene oxide polymers, carboxylic acid esters, polysiloxanes, polyol aliphatic esters, and the like.

As described, the lubricating oil is thickened to a grease with a suitable substituted urea compound or mixture of substituted-urea compounds. These ureido compounds, their definitions, their methods of preparation and the methods of thickening oils with these compounds are disclosed in the prior art including the above-identified patents, the disclosures of which are incorporated herein by reference. These thickeners can be represented by the general formula $$R.NH-CO.NH.R''.NH)_xCO.NH.R' \qquad (2)$$

wherein x is an integer from 0 to about 7, preferably from 1 to about 3; R and R' can be the same or different hydrocarbyl selected from aliphatic, aromatic, alicyclic and combinations thereof having from 1 to about 30 carbon atoms, preferably having from about 6 to about 20 carbon atoms and R'' is hydrocarbylene selected from aliphatic, aromatic, alicyclic and combinations thereof having from 2 to about 30 carbon atoms, preferably having from about 2 to about 18 carbon atoms. When x is greater than 1, the various hydrocarbylene groups can be the same or different. The expressions aliphatic, aromatic, alicyclic and combinations thereof used in defining R, R' and R'', are intended to include the presence of substituents including alkyl, aryl, halogen, alkoxy, carboalkoxy, hydroxy, carboxy, nitro, cyano, sulfonyl, amido, sulfonamide, and the like, and the term aromatic further is intended to include polynuclear aromatic, condensed polynuclear aromatic, and the like, all as described in the above-identified prior art.

A ureido thickener of particular suitability for use in greases subjected to elevated temperatures is the aryldiurea composition described in U.S. Pat. No. 4,065,395. This thickener is prepared by reacting a mixture of p-toluidine and p-chloroaniline at a mol ratio between about 3:1 and 17:1 with a toluene diisocyanate at a mol ratio of two mols of aryl amine for each mol of the toluene diisocyanate.

These ureido thickeners are conveniently prepared, as described in the above-mentioned patents by the reaction of an appropriate combination of one or more monoamines and/or diamines with one or more monoisocyanates and/or diisocyanates to produce the desired composition. These amine and isocyanate reactants are brought together at an appropriate temperature in a suitable solvent with the lubricating oil itself being the preferred reaction solvent.

The amount of the substituted-urea thickener that is used is an amount sufficient to thicken the lubricating oil to the consistency of grease. Generally, at least about five percent of the thickener is used and preferably at least about ten percent. The maximum amount of the thickener that is used is about 50 percent and preferably a maximum of about 30 percent is used.

The grease composition of the present invention can contain other grease additives, as desired, in appropriate quantities to modify or improve other properties or characteristics of the grease. Thus, the grease can contain one or more additives selected from the following list: antioxidants, dispersants, anticorrosion agents, rust inhibitors, metal deactivators, antiwear agents, other extreme pressure agents, tackiness agents, dyes, and the like.

DESCRIPTION OF PREFERRED EMBODIMENTS

EXAMPLE 1

The preparation of a tetrahydrocarbyl-ammonium thiomolybdate from a water-insoluble tetrahydrocarbylammonium salt in a two-phase reaction is described. A 360 g quantity of a commercial mixture containing 75 percent dicocodimethylammonium chloride (0.615 mol) and 25 percent isopropanol was dissolved in one liter of toluene and this solution was stirred with an aqueous solution containing 102 g (0.337 mol) of potassium thiomolybdate in one liter of water at room temperature for 30 minutes. After separating out the dark red toluene layer and water washing it, the toluene was removed under reduced pressure. A quantitative yield of semi-solid, dark red dicocodimethylammonium thiomolybdate was obtained. Analysis of the product for thiomolybdate ion by infrared spectroscopy showed a band at 460 cm$^{-1}$ and by ultraviolet-visible spectroscopy in toluene showed a band at 470 nm. The calculated elemental analysis for dicocodimethylammonium thiomolybdate was N, 2.7%, S, 12.2% and Mo, 9.15%. The actual elemental analysis was N, 2.63%, S, 12.44% and Mo, 9.3%.

EXAMPLE 2

The preparation of a different tetrahydrocarbylammonium thiomolybdate is described. A solution containing 120 g (0.297 mol) of trioctylmethylammonium chloride in 800 ml of toluene was vigorously stirred for 30 minutes with a solution containing 51 g (0.168 mol) of potassium thiomolybdate in 500 ml of water. Following the reaction the toluene layer was separated and the toluene was removed at reduced pressure. There was a quantitative recovery of the red viscous trioctylmethylammonium thiomolybdate.

EXAMPLES 3-6

A grease, thickened with an aryldiurea thickening composition, was tested for its extreme pressure properties by the Timken Test, ASTM D2509, before and after the addition of several quaternary ammonium thiomolybdates (QATM). The grease was thickened by reacting p-toluidine, p-chloroaniline and toluene diisocyanate in the lubricating oil in a mol ratio of 7:1:4. The grease composition before addition of the thiomolybdate contained 75 weight percent of a heavy neutral oil, 20 percent of the aryldiurea thickener, 0.5 percent of an oxidation inhibitor, 0.5 percent of a rust inhibitor and four percent of precipitated calcium carbonate to improve the e.p. properties and extend the functional life of the grease. After the base grease was heated to 200° F. for one hour, the quaternary ammonium thiomolybdate was added and mixed in with a power-driven beater. The results of the Timken Tests (OK value) on the various compositions are set out in Table II.

TABLE II

| Example | 3 | 4 | 5 | 6 |
|---|---|---|---|---|
| Grease, wt. % | 100 | 99 | 8 | 98 | 98 |
| QATM, wt. % | | | | |
| trioctylmethyl | | 1 | 2 | |
| dicocodimethyl | | | 2 | |
| trialkylmethyl$^a$ | | | | 2 |
| ASTM D2509, lbs. | 30 | 60 | 60 | 50 | 60 |

$^a$alkyl is a mixture of 8 and 10 carbon atom alkyl groups

EXAMPLE 7

Tetramethylammonium thiomolybdate was tested in a different batch of the grease described in the preceding examples. The grease measured 35 pounds (OK value) by the Timken Test, ASTM D2509, prior to the addition of the thiomolybdate and 35 pounds after the addition of two percent tetramethylammonium thiomolybdate to the grease, demonstrating that this thiomolybdate exerts no improvement on the extreme pressure properties of the grease.

EXAMPLE 8

Another portion of the trioctylmethylammonium thiomolybdate prepared as described in Example 2 and utilized in Example 3 was tested in a commercial grease thickened with a lithium soap. The grease contained 40.1 weight percent medium neutral oil, 51 percent 150 MC bright stock, seven percent of the lithium soap, 0.67 percent glycerin, one percent of an oxidation inhibitor and 0.25 percent of a rust inhibitor. This grease tested ten pounds (OK value) as the maximum load by the Timken Test with no thiomolybdate and ten pounds in each of two samples of the test grease containing, respectively, one percent and two percent trioctylmethylammonium thiomolybdate.

EXAMPLE 9

Example 8 was repeated using two percent trioctylmethylammonium thiomolybdate in a commercial grease thickened with a calcium soap (Witco Cup Grease No. 2). This grease tested five pounds (OK value) as the maximum load by the Timken Test with no thiomolybdate present and five pounds with two percent trioctylmethyl-ammonium thiomolybdate in the grease.

The final three examples demonstrate that certain tetraalkylammonium thiomolybdates, containing a relatively low total number of carbon atoms, are ineffective for improving the extreme pressure properties of greases thickened with substituted-urea thickeners and that tetraalkylammonium thiomolybdates which are very effective in improving the extreme pressure properties of greases thickened with substituted-urea thickeners are ineffective in improving the extreme pressure properties of greases thickened with alkali metal soaps and alkaline earth metal soaps.

It is to be understood that the above disclosure is by way of specific example and that numerous modifications and variations are available to those of ordinary skill in the art without departing from the true spirit and scope of the invention.

We claim:

1. A grease composition comprising a hydrocarbon lubricating oil thickened to a grease with a substituted-urea thickener and a quantity sufficient to improve the extreme pressure properties of the grease of a tetrahydrocarbylammonium thiomolybdate or a mixture thereof having the formula

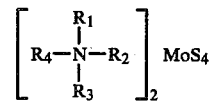

wherein $R_1$, $R_2$ and $R_3$ are independently selected from straight and branched alkyl and alkenyl having from one to about 30 carbon atoms, $R_4$ is selected from straight and branched alkyl or alkenyl having from about 4 to about 30 carbon atoms and benzyl, and the total number of carbon atoms in $R_1$, $R_2$, $R_3$ and $R_4$ is between about 15 and about 80 carbon atoms.

2. A grease composition in accordance with claim 1 wherein $R_1$, $R_2$, $R_3$ and $R_4$ independently have from about 4 to about 20 carbon atoms, and the total number of carbon atoms in $R_1$, $R_2$, $R_3$ and $R_4$ is between about 20 and about 60 carbon atoms.

3. A grease composition in accordance with claim 1 wherein $R_1$ and $R_2$ are methyl and $R_3$ and $R_4$ independently have between about 12 and about 20 carbon atoms.

4. A grease composition in accordance with claim 3 wherein said thiomolybdate comprises dicocodimethylammonium thiomolybdate.

5. A grease composition in accordance with claim 1 wherein $R_1$ is methyl; $R_2$, $R_3$ and $R_4$ independently have between about 4 and about 20 carbon atoms and the total number of carbon atoms in $R_1$, $R_2$, $R_3$ and $R_4$ is between about 15 and about 60.

6. A grease composition in accordance with claim 5 wherein said thiomolybdate comprises trioctylmethylammonium thiomolybdate.

7. A grease composition in accordance with claim 5 wherein $R_1$ is methyl and $R_2$, $R_3$ and $R_4$ independently have between about 12 and about 20 carbon atoms.

8. A grease composition in accordance with claim 1 comprising from about 0.1 to about ten weight percent of said tetrahydrocarbylammonium thiomolybdate.

9. A grease composition in accordance with claim 1 comprising from about 0.5 to about five weight percent of said tetrahydrocarbylammonium thiomolybdate.

10. A grease composition in accordance with claim 1 wherein said substituted-urea thickener has the formula

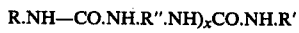
R.NH—CO.NH.R''.NH)$_x$CO.NH.R' wherein x is an integer from 0 to about 7, R and R' are the same or different hydrocarbyl groups selected from aliphatic, aromatic, alicyclic, and combinations thereof, having from 1 to about 30 carbon atoms, and R'' is hydrocarbylene selected from aliphatic, aromatic, alicyclic and combinations thereof, having from 2 to about 30 carbon atoms.

11. A grease composition in accordance with claim 10 wherein x is an integer from 1 to about 3, R and R' have from about 6 to about 20 carbon atoms, and R'' has from about 2 to about 18 carbon atoms.

12. A grease composition in accordance with claim 10 wherein x is 1 and R, R' and R'' are aromatic having from 6 to about 8 carbon atoms.

13. A grease composition in accordance with claim 12 wherein R and R' are a mixture of p-tolyl and p-chlorophenyl in a ratio of about 3:1 to about 17:1 and R'' is toluylene, $CH_3C_6H_3=$.

14. A grease composition in accordance with claim 10 comprising from about 5 to about 50 weight percent of said substituted-urea thickener.

15. A grease composition in accordance with claim 14 comprising from about 10 to about 30 weight percent of said substituted-urea thickener.

16. A grease composition in accordance with claim 1 in which the total number of carbon atoms in $R_1$, $R_2$, $R_3$ and $R_4$ is between about 24 and about 80 carbon atoms.

* * * * *